US012616598B2

(12) United States Patent (10) Patent No.: US 12,616,598 B2
Seymour et al. (45) Date of Patent: May 5, 2026

(54) COMBINATION SURGICAL KIT AND HAND RESTRAINT

(71) Applicant: Trice Medical, Inc., Malvern, PA (US)

(72) Inventors: Stuart Seymour, Malvern, PA (US);
Richard Thomas Briganti,
Philadelphia, PA (US); **Alfred J.
Intintoli**, West Chester, PA (US);
Stefanie Hurowitz, Malvern, PA (US);
Tyler Bryant, Malvern, PA (US)

(73) Assignee: Trice Medical, Inc., Malvern, PA (US)

( * ) Notice: Subject to any disclaimer, the term of this
patent is extended or adjusted under 35
U.S.C. 154(b) by 651 days.

(21) Appl. No.: 17/417,057

(22) PCT Filed: Dec. 20, 2019

(86) PCT No.: PCT/US2019/068116
§ 371 (c)(1),
(2) Date: Jun. 21, 2021

(87) PCT Pub. No.: WO2020/142289
PCT Pub. Date: Jul. 9, 2020

(65) Prior Publication Data
US 2022/0071795 A1 Mar. 10, 2022

Related U.S. Application Data

(60) Provisional application No. 62/894,366, filed on Aug.
30, 2019, provisional application No. 62/799,333,
(Continued)

(51) Int. Cl.
*A61F 5/37* (2006.01)
*A61B 50/20* (2016.01)
*A61F 15/00* (2006.01)

(52) U.S. Cl.
CPC ............ *A61F 5/3761* (2013.01); *A61B 50/20*
(2016.02); *A61F 15/001* (2013.01)

(58) Field of Classification Search
CPC .... A61F 5/0118; A61F 5/013; A61F 5/05858;
A61F 5/05866; A61F 5/05875;
(Continued)

(56) References Cited

U.S. PATENT DOCUMENTS 2,266,231 A * 12/1941 Mazzeo ................. A61M 5/52
128/877
2,569,080 A 9/1951 Trimble et al.
(Continued)

FOREIGN PATENT DOCUMENTS

DE 29521451 5/1997
DE 202 10 952 12/2002
(Continued)

OTHER PUBLICATIONS

International Search Report and Written Opinion of PCT/US2019/
068116, dated Apr. 3, 2020, in 14 pages.
(Continued)

*Primary Examiner* — Adam Baker
(74) *Attorney, Agent, or Firm* — Knobbe, Martens, Olson
& Bear LLP

(57) ABSTRACT

The present invention relates to a combination surgical kit.
The surgical kit can include a plurality of tools for a medical
procedure, the plurality of tools including a first set of tools
and a second set of tools. The surgical kit can also include
a hand/wrist positioning tray device, including a bottom tray
configured to hold the first set of tools, a middle tray
configured to hold the second set of tools; and a top tray
including a recess configured to receive a patients hand for
the medical procedure.

14 Claims, 8 Drawing Sheets

Related U.S. Application Data filed on Jan. 31, 2019, provisional application No. 62/788,078, filed on Jan. 3, 2019.

(58) Field of Classification Search
CPC .. A61F 5/10; A61F 5/37; A61F 5/3761; A61F 17/00; A61F 15/001; A61G 13/1235; A61G 13/124; A61G 13/1285; A61G 13/129; A61G 13/0045; A61B 50/33; A61B 50/34; A61B 50/36; A61B 50/362; A61B 2050/3002–3015; A61B 50/20
USPC ........................................................ 128/845
See application file for complete search history.

(56) References Cited

U.S. PATENT DOCUMENTS

| | | | |
|---|---|---|---|
| 3,198,197 A * | 8/1965 | Van Halanger ...... A45D 29/004 | |
| | | | 132/73 |
| 3,592,193 A | 7/1971 | Higgins | |
| 3,797,505 A | 3/1974 | Gilhaus | |
| 4,901,717 A | 2/1990 | Moore et al. | |
| 5,089,000 A | 2/1992 | Agee et al. | |
| 5,176,695 A | 1/1993 | Dulebohm | |
| 5,253,659 A | 10/1993 | McNamara | |
| 5,273,024 A | 12/1993 | Menon et al. | |
| 5,282,816 A | 2/1994 | Miller et al. | |
| 5,306,284 A | 4/1994 | Agee et al. | |
| 5,318,582 A | 6/1994 | Chow | |
| 5,323,765 A * | 6/1994 | Brown ........... A61B 17/320036 | |
| | | | 600/109 |
| 5,325,883 A | 7/1994 | Orr | |
| 5,353,812 A | 10/1994 | Chow | |
| 5,366,465 A | 11/1994 | Mirza | |
| 5,387,222 A | 2/1995 | Strickland | |
| 5,387,223 A | 2/1995 | Agee | |
| 5,397,320 A | 3/1995 | Essig et al. | |
| 5,437,662 A | 8/1995 | Nardella | |
| D364,456 S | 11/1995 | Solnit et al. | |
| 5,472,415 A | 12/1995 | King et al. | |
| 5,480,408 A | 1/1996 | Chow | |
| 5,522,897 A | 6/1996 | King et al. | |
| 5,569,283 A | 10/1996 | Green et al. | |
| 5,569,292 A | 10/1996 | Scwemberger et al. | |
| 5,620,446 A | 4/1997 | McNamara | |
| D381,747 S | 7/1997 | Kapec et al. | |
| 5,649,946 A | 7/1997 | Bramlet | |
| 5,651,790 A | 7/1997 | Resnick et al. | |
| 5,658,300 A | 8/1997 | Bito et al. | |
| 5,732,821 A * | 3/1998 | Stone ..................... A61B 50/30 | |
| | | | 206/439 |
| 5,752,972 A | 5/1998 | Hoogeboom | |
| 5,759,150 A | 6/1998 | Konou et al. | |
| 5,779,364 A | 7/1998 | Cannelongo et al. | |
| 5,782,850 A | 7/1998 | Ro | |
| 5,817,127 A | 10/1998 | Borodulin | |
| 5,827,311 A | 10/1998 | Berelsman et al. | |
| 5,827,312 A | 10/1998 | Brown | |
| 5,845,643 A * | 12/1998 | Vergano .............. A61F 5/05866 | |
| | | | 128/877 |
| 5,893,861 A | 4/1999 | Yumoto | |
| 5,902,315 A | 5/1999 | DuBois | |
| 5,908,433 A | 6/1999 | Eager et al. | |
| 5,931,304 A * | 8/1999 | Hammond .............. A61F 17/00 | |
| | | | 206/570 |
| 5,957,944 A | 9/1999 | Khuri et al. | |
| 5,993,459 A | 11/1999 | Larsen et al. | |
| 6,007,554 A | 12/1999 | Van Ess | |
| 6,019,774 A | 2/2000 | Weiss et al. | |
| 6,030,406 A | 2/2000 | Davis et al. | |
| 6,077,221 A * | 6/2000 | Fowler, Jr. ......... A61B 17/0293 | |
| | | | 600/233 |
| 6,106,539 A | 8/2000 | Fortier | |
| 6,148,522 A | 11/2000 | Dobandi | |
| 6,179,852 B1 | 1/2001 | Strickland et al. | |
| 6,193,653 B1 | 2/2001 | Evans et al. | |
| 6,193,671 B1 | 2/2001 | Turturro et al. | |
| 6,254,555 B1 | 7/2001 | Sevier et al. | |
| D453,829 S | 2/2002 | McMahon et al. | |
| 6,432,047 B1 | 8/2002 | Gust et al. | |
| 6,447,509 B1 | 9/2002 | Bonnet et al. | |
| D483,870 S | 12/2003 | Scheller et al. | |
| 6,755,815 B2 | 6/2004 | Schultz | |
| D497,669 S | 10/2004 | Blanco | |
| D511,002 S | 10/2005 | Easley | |
| 6,960,164 B2 | 11/2005 | O'Heeron | |
| 6,972,027 B2 | 12/2005 | Fallin et al. | |
| D517,694 S | 3/2006 | Wilshire et al. | |
| D525,361 S | 7/2006 | Hushka | |
| 7,141,214 B2 | 11/2006 | Puntambekar | |
| D538,425 S | 3/2007 | Awh | |
| D546,948 S | 7/2007 | Huttner | |
| 7,303,561 B2 | 12/2007 | Garrison et al. | |
| D581,050 S | 11/2008 | Cottier | |
| D590,945 S | 4/2009 | Berberich | |
| 7,686,838 B2 | 3/2010 | Wolf et al. | |
| 7,739,799 B2 | 6/2010 | Van Deursen | |
| D629,901 S | 12/2010 | Palmer et al. | |
| D629,902 S | 12/2010 | Palmer et al. | |
| D636,874 S | 4/2011 | Palmer et al. | |
| D638,940 S | 5/2011 | Palmer et al. | |
| 8,252,011 B1 | 8/2012 | Forrester | |
| 8,273,098 B2 | 9/2012 | Strickland | |
| 8,382,804 B2 | 2/2013 | Thomke et al. | |
| 8,398,397 B2 | 3/2013 | Fischer | |
| 8,434,491 B2 * | 5/2013 | Born ................... A61G 13/1235 | |
| | | | 128/845 |
| 8,579,930 B2 | 11/2013 | Palmer et al. | |
| 8,672,960 B2 | 3/2014 | Briganti et al. | |
| 8,771,303 B1 | 7/2014 | Jurbala | |
| 9,028,516 B2 | 5/2015 | Palmer et al. | |
| 10,206,703 B2 | 2/2019 | Palmer et al. | |
| 10,219,826 B2 | 3/2019 | Seymour et al. | |
| 10,245,062 B2 | 4/2019 | Seymour | |
| 11,000,303 B2 | 5/2021 | Seymour | |
| 2002/0091355 A1 | 7/2002 | Hayden | |
| 2003/0028147 A1 | 2/2003 | Aves | |
| 2004/0054378 A1 | 3/2004 | Yang | |
| 2004/0243157 A1 | 12/2004 | Connor et al. | |
| 2004/0267243 A1 | 12/2004 | Klotz | |
| 2005/0021048 A1 | 1/2005 | Kuhlman | |
| 2005/0096646 A1 | 5/2005 | Wellman | |
| 2006/0030863 A1 | 2/2006 | Fields | |
| 2006/0149267 A1 | 7/2006 | Nordt | |
| 2006/0178682 A1 | 8/2006 | Boehlke | |
| 2006/0190021 A1 | 8/2006 | Hausman et al. | |
| 2006/0241665 A1 | 10/2006 | Bosley | |
| 2006/0272979 A1 | 12/2006 | Lubbers | |
| 2006/0276782 A1 | 12/2006 | Gedebou | |
| 2007/0106295 A1 | 5/2007 | Garrison | |
| 2007/0215001 A1 | 9/2007 | Voegele | |
| 2007/0288043 A1 | 12/2007 | Rehnke | |
| 2008/0045989 A1 | 2/2008 | Welborn | |
| 2008/0255600 A1 | 10/2008 | Braam et al. | |
| 2009/0018568 A1 | 1/2009 | Bacher | |
| 2009/0048620 A1 | 2/2009 | Weiss et al. | |
| 2009/0163963 A1 | 6/2009 | Berrevoets | |
| 2009/0270856 A1 | 10/2009 | Saadat et al. | |
| 2010/0069936 A1 | 3/2010 | Palmer et al. | |
| 2010/0094315 A1 | 4/2010 | Beardsley et al. | |
| 2010/0228085 A1 | 9/2010 | Mirza et al. | |
| 2011/0046652 A1 | 2/2011 | Rehnke | |
| 2011/0087255 A1 | 4/2011 | McCormack et al. | |
| 2011/0087258 A1 | 4/2011 | Sluss | |
| 2011/0252651 A1 | 10/2011 | Sewell | |
| 2011/0306996 A1 | 12/2011 | McCormack et al. | |
| 2012/0016397 A1 | 1/2012 | Briganti et al. | |
| 2014/0031848 A1 | 1/2014 | Mirza | |
| 2014/0052166 A1 | 2/2014 | Haindl | |
| 2014/0088518 A1 | 3/2014 | Knapp | |
| 2014/0094798 A1 | 4/2014 | Garrison | |
| 2014/0097227 A1 | 4/2014 | Aronhalt | |
| 2014/0107686 A1 | 4/2014 | Duperier | |
| 2014/0336581 A1 | 11/2014 | Collin | |

(56)  References Cited

U.S. PATENT DOCUMENTS

| | | | |
|---|---|---|---|
| 2015/0034695 A1 | 2/2015 | Kapadia |
| 2015/0306352 A1 | 10/2015 | Banerian |
| 2016/0015447 A1 | 1/2016 | Rosa |
| 2016/0058437 A1 | 3/2016 | Penna |
| 2016/0128714 A1 | 5/2016 | DaSilva |
| 2016/0157881 A1 | 6/2016 | Seymour et al. |
| 2016/0345998 A1 | 12/2016 | Seymour |
| 2016/0354105 A1 | 12/2016 | Seymour |
| 2017/0173306 A1 | 6/2017 | Kumar |
| 2017/0348467 A1 | 12/2017 | Park |
| 2018/0008302 A9 | 1/2018 | Seymour |
| 2019/0159797 A1 | 5/2019 | Seymour et al. |
| 2019/0167293 A1 | 6/2019 | Seymour et al. |

FOREIGN PATENT DOCUMENTS

| | | |
|---|---|---|
| EP | 2358281 | 7/2018 |
| JP | 2007244493 | 9/2007 |
| WO | WO 97/42887 | 11/1997 |
| WO | WO 98/034548 | 8/1998 |
| WO | WO 2015/081231 | 6/2015 |
| WO | WO 2015/081281 | 6/2015 |
| WO | WO 2020/142289 | 7/2020 |

OTHER PUBLICATIONS

Australian Office Action regarding Application No. 20191419456, dated Jul. 18, 2024, 3 pages.

* cited by examiner

COMBINATION SURGICAL KIT AND HAND RESTRAINT

CROSS-REFERENCE TO RELATED APPLICATIONS

This application claims priority to U.S. Provisional Application No. 62/788,078, entitled COMBINATION SURGICAL KIT AND HAND RESTRAINT, filed on Jan. 3, 2019. This application also claims priority to U.S. Provisional Application No. 62/799,333, entitled SURGICAL INSTRUMENT, filed on Jan. 31, 2019. This application also claims priority to U.S. Provisional Application No. 62/894,366, entitled COMBINATION SURGICAL KIT AND HAND RESTRAINT, filed on Aug. 30, 2019. The entirety of each of these applications is hereby incorporated by reference in its entirety.

FIELD OF INVENTION

The invention pertains to methods, apparatus, and systems for performing hand surgeries such as an endoscopic ligament release surgery, carpal tunnel release, plantar fasciotomy, gastroc release, cubital tunnel release, and tarsal tunnel release surgery, and similar surgical procedures on anatomic members.

BACKGROUND

Hand surgery is a common medical procedure in the United States and throughout the world. During surgeries such as endoscopic ligament release surgery, carpal tunnel release, plantar fasciotomy, gastroc release, cubital tunnel release, and tarsal tunnel release, the hand/wrist of the patient is positioned on an operating table whereupon various surgical instruments are employed to achieve the desired surgical goal. Conventionally, the medical staff assisting the surgeon will discern the surgical instruments required for a scheduled patient surgery, have them sterilized at a central processing area and once received back, position them in the sterile field in the operating room. The surgeon thereafter will employ the staff-gathered sterilized instruments during various stages of the hand surgery procedure.

Different surgical interventions on the various internal parts of the hand and wrist generally may require certain instruments common to all such surgeries. However, customized surgical instruments may also be required which are specifically adapted to perform each different intricate specific surgical procedure. It is conventionally left up to the surgical support staff to discern both the common and customized surgical instruments to gather, sterilize, and position in the operating room, in anticipation of the surgeon needing them during a schedule procedure. Should the support staff err in selection of the instruments needed for a particular surgery, the required instruments must be retrieved during the surgery for the surgeon.

A further consideration is the positioning of the surgical site, therefore the static positioning of the hand and wrist of the patient during the length of the procedure must be ensured. Should a patient move their arm or hand during the surgical procedure, the results can be catastrophic, potentially leading to further tissue damage. Conventionally, table stands with straps or retaining members are employed for such a purpose. Such stands and straps must also be sterilized in advance of the procedure to maintain the sterile field during the surgery.

For specialized surgery to the hand and wrist, it is important that the hand and wrist of the patient be restrained to prevent movement. Additionally, for a quick and successful surgery it is important that the correct sterilized surgical instruments needed for the particular procedure be present in the operating room and ready for use by the surgeon. This is important when transitioning procedures from the operating room with ready access to sterilization services to procedure rooms and office clinics where such services might not be readily available.

The forgoing examples of related art as to surgical kits including customized instruments to the task and hand restraints, and limitations related therewith, are intended to be illustrative and not exclusive, and they do not imply any limitations on the invention described and claimed herein. Various limitations of the related art will become apparent to those skilled in the art upon a reading and understanding of the specification below and the accompanying drawings.

SUMMARY OF THE INVENTION

The device herein provides a solution to the shortcomings of conventional surgery to and through the hand and wrist, which rely on staff to discern the instruments required, sterilize the instruments, and pre-position the instruments. The device provides a customized set of instruments adapted to perform the specific surgery on a patient in a single container. Additionally, the container includes a hand restraint for the hand of the patient on which the surgery will be performed. Still further, a drape cloth conventionally employed by most surgeons is also included.

Each container may be labeled for the specific surgery to which it, and the instruments, and hand mount within are adapted. Provided sterile in a sealed envelope or box or both, the resulting surgical kit is customized with the instruments required for the specific surgery to be performed, thereby alleviating mistakes by inexperienced surgical staff in surgical preparations. Further, the hand and wrist restraint can be formed for a single hand, or, may be configured to provide a mount to either hand of the patient thereby alleviating another issue which can arise should the correct restraint not be provided in advance.

With respect to the above description, before explaining at least one preferred embodiment of the herein disclosed combination surgical kit and hand restraint in detail, it is to be understood that the disclosed surgical system herein is not limited in its application to the details of construction and to the arrangement of the components in the following description or illustrated in the drawings. The examples described herein are capable of other embodiments and of being practiced and carried out in various ways which will be obvious to those skilled in the art. Also, it is to be understood that the phraseology and terminology employed herein are for the purpose of description and should not be regarded as limiting.

As such, those skilled in the art will appreciate that the conception upon which this disclosure is based may readily be utilized as a basis for designing of other structures, methods and systems for carrying out the several purposes of the present disclosed customized surgical kit with hand restraint. It is important, therefore, that the claims be regarded as including such equivalent construction and methodology insofar as they do not depart from the spirit and scope of the present invention.

The objects features, and advantages of the present invention, as well as the advantages thereof over existing prior art, which will become apparent from the description to follow, are accomplished by the improvements described in this specification and hereinafter described in the following detailed description which fully discloses the invention, but should not be considered as placing limitations thereon.

In some aspects, a combination surgical kit includes a plurality of sterile tools for a medical procedure, the plurality of tools comprising a first set of tools and a second set of tools; and a hand positioning tray device. The hand positioning tray may include a bottom tray configured to hold the first set of tools, a middle tray configured to hold the second set of tools, and a top tray comprising a recess configured to receive a patient's hand for the medical procedure.

The first set of tools can include one or more selected from the group consisting of: guides, a retrograde blade, and a combination probe and rasp instrument. The combination probe and rasp instrument can include two different surgical tools extending from respective opposing ends of a centrally located handle. The second set of tools can include one or more selected from the group consisting of: a scalpel blade, a pair of scissors, forceps, a dilator and elevator tool, or a retractor. The bottom tray can include a plurality of recesses configured to receive each of the first set of tools. The middle tray can include a plurality of recesses configured to receive each of the second set of tools. The top tray can include a recess dimensioned to receive the patient's hand. The top tray can include a first elevated portion to support a patient's wrist. The first elevated portion can include a roll of bandages. The top tray can include a strap configured to be positioned over and restrain the patient's hand.

In some examples, a hand positioning tray device can include a bottom tray configured to hold a first set of tools, a middle tray configured to hold a second set of tools; and a top tray comprising a recess configured to receive a patient's hand for a medical procedure. The first set of tools can include one or more selected from the group consisting of: guides, a retrograde blade, and a combination probe and rasp instrument. The combination probe and rasp instrument can include two different surgical tools extending from respective opposing ends of a centrally located handle. The second set of tools can include one or more selected from the group consisting of: a scalpel blade, a pair of scissors, forceps, a dilator and elevator tool, or a retractor. The bottom tray can include a plurality of recesses configured to receive each of the first set of tools. The middle tray can include a plurality of recesses configured to receive each of the second set of tools. The top tray can include a recess dimensioned to receive the patient's hand. The top tray can include a first elevated portion to support a patient's wrist. The first elevated portion can include a roll of bandages or esmark for positioning the patient's wrist. The top tray can include an elastomer strap configured to be positioned over and restrain the patient's hand.

In some aspects, a method of positioning a hand for a medical procedure can include providing a hand positioning device comprising a top tray, the top tray comprising a substantially flat surface and an elevated portion; positioning a patient's wrist on the elevated portion of the top tray; and positioning a patient's hand on the substantially flat surface of the top tray. The method can further include securing the patient's hand to the top tray by positioning a strap of the top tray over the patient's hand. The method can further include positioning a plurality of tools in a bottom tray. The plurality of tools can include guides, a retrograde blade, and a combination probe and rasp instrument. The combination probe and rasp instrument can include two different surgical tools extending from respective opposing ends of a centrally located handle. The hand positioning device can further include a middle tray. The method can further include positioning a plurality of tools in the middle tray. The plurality of tools can include a scalpel blade, a pair of scissors, forceps, a dilator and elevator tool, or a retractor.

BRIEF DESCRIPTION OF THE DRAWINGS

The accompanying drawings, which are incorporated herein and form a part of the specification, illustrate some, but not the only or exclusive, examples of embodiments and/or features of the invention. It is intended that the embodiments and figures disclosed herein are to be considered illustrative rather than limiting. In the drawings.

Figure 1:
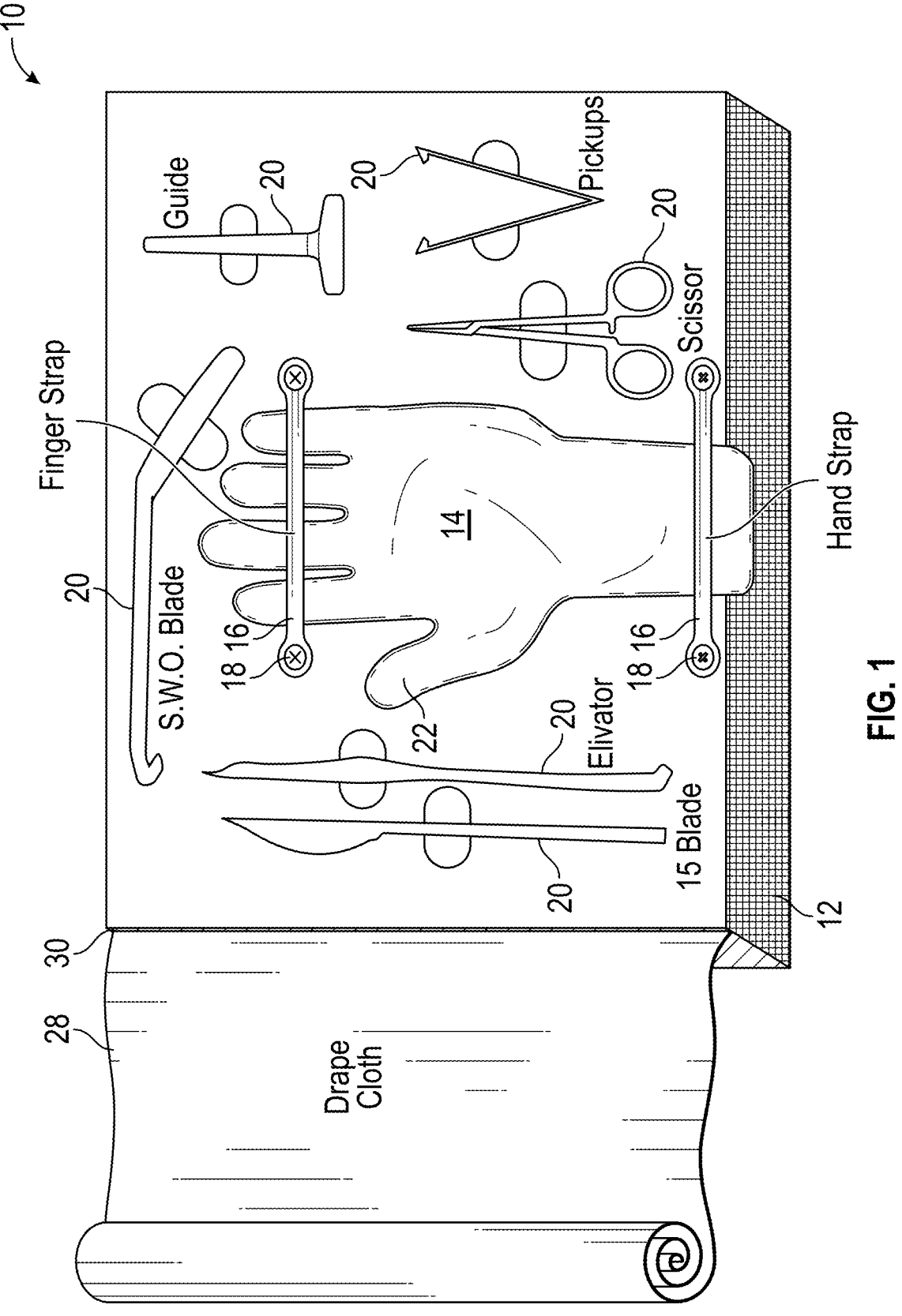
FIG. 1 is a diagram illustrating one example of the device herein wherein a polymeric mount is configured to hold the individual instruments required for a specific surgical procedure and a recess formed on or into the mount provides a means to position and secure the hand and wrist to prevent movement during the procedure.

Other aspects of the present invention will be more readily understood when considered in conjunction with the accompanying drawings, and the following detailed description, neither of which should be considered limiting.

DETAILED DESCRIPTION OF THE INVENTION

Embodiments disclosed in this section or elsewhere in this application relate to devices and methods for positioning a patient's hand for minimally invasive tissue visualization and access, including endoscopic procedures.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the terms "about," "around," and "approximately." These terms are used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

In this description, the directional prepositions of up, upwardly, down, downwardly, front, back, top, upper, bottom, lower, left, right and other such terms refer to the nose engagement device as it is oriented and appears in the drawings and are used for convenience only; they are not intended to be limiting or to imply that the device has to be used or positioned in any particular orientation.

Figure 2:
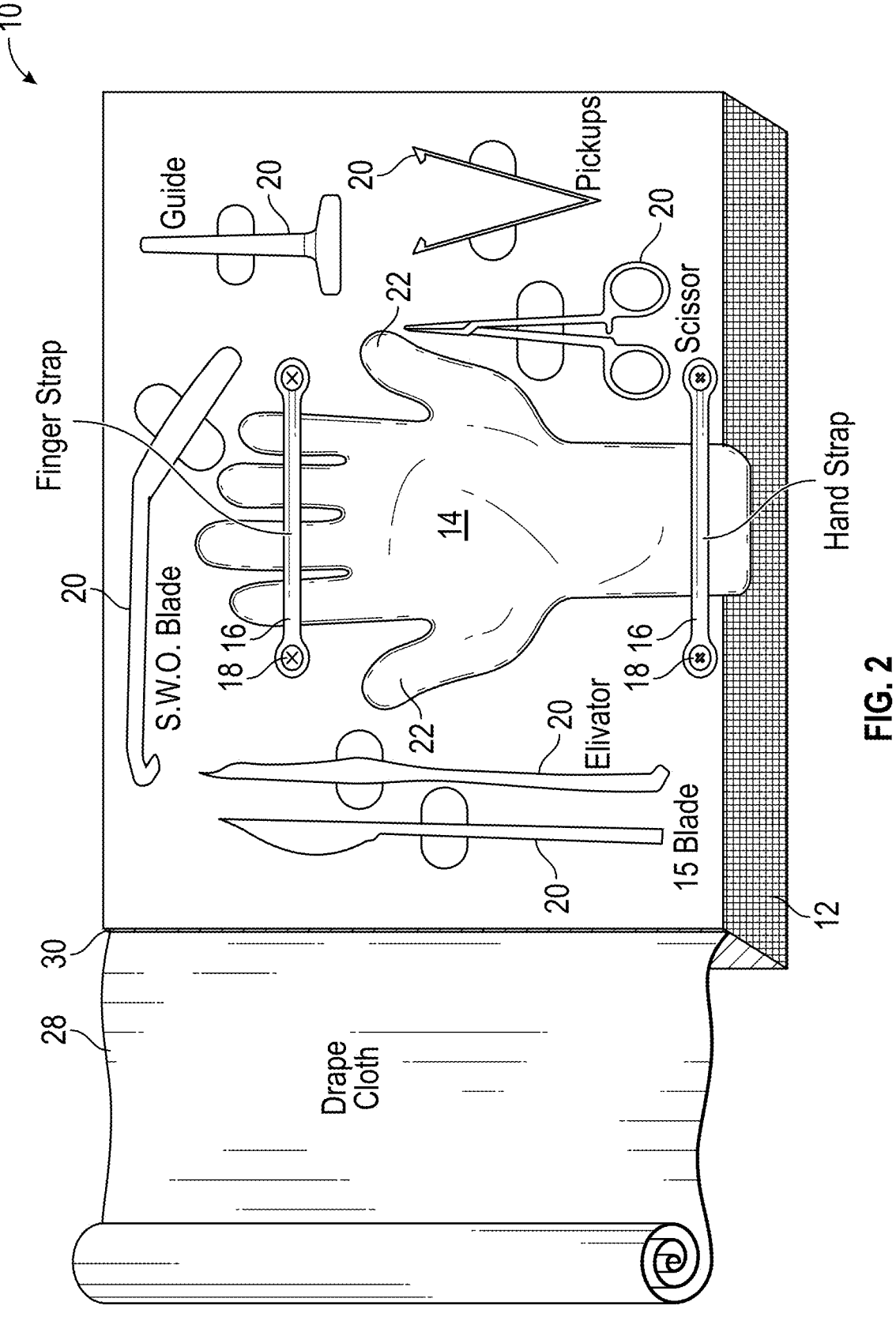
FIG. 2 is another example of the device herein wherein the recess adapted for positioning and stabilizing a hand to prevent movement, is adapted for either hand of the patient through opposing thumb recesses positioned thereon.
Figure 3:
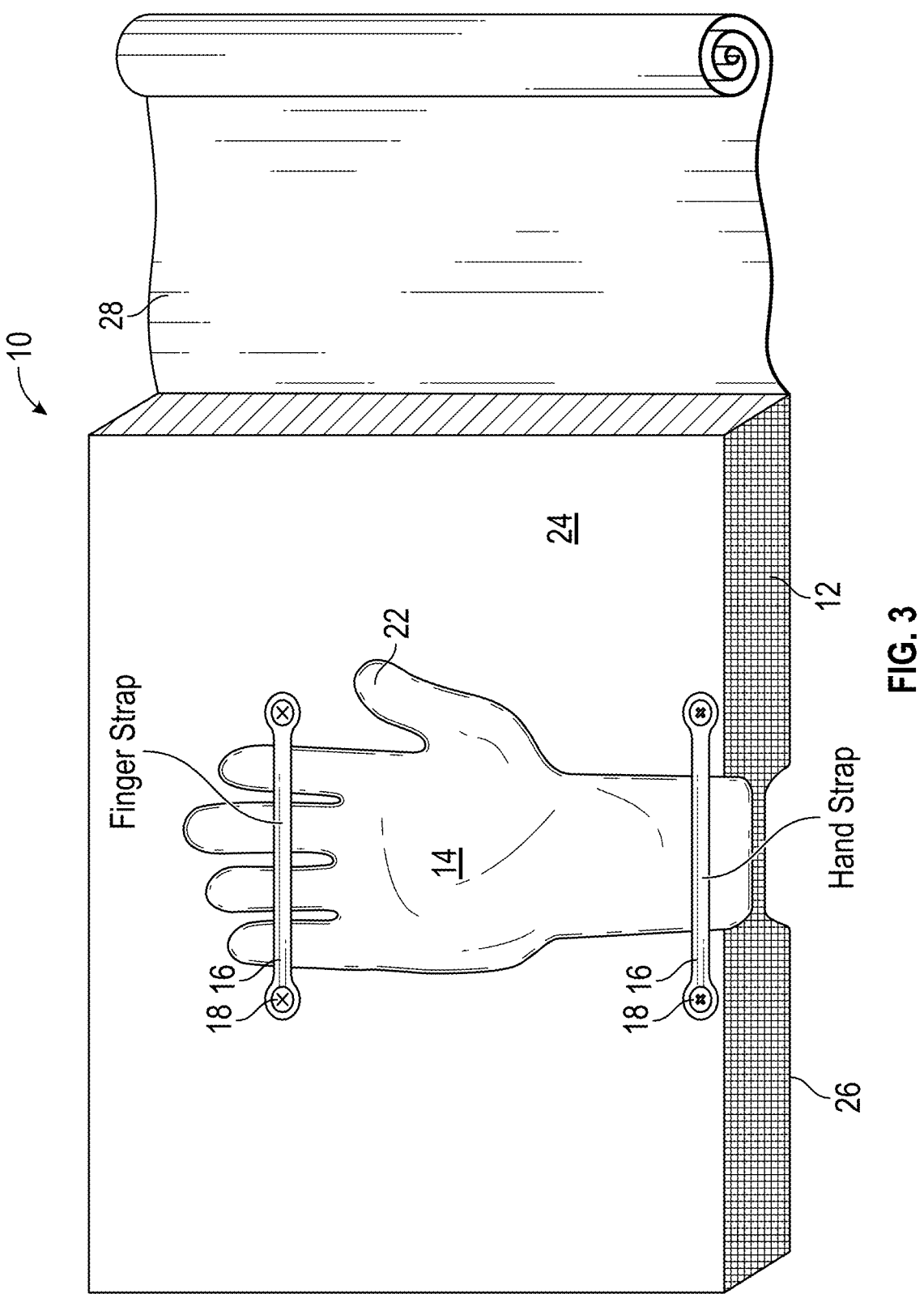
FIG. 3 depicts another example of the device herein, where a mounting recess is positioned on a first side of the polymeric mount for one hand, and on the opposite side for the opposite hand of a patient.

Now referring to the examples of FIGS. 1-3, there can be seen in FIG. 1 an overhead view of one example of the surgical kit device 10 herein which includes a polymeric mount 12. The mount 12 may be formed of a material which may be sterilized by conventional methods such as PETG, Polyesters, Fluoropolymers, high temperature thermoplastics, silicone, PGA, polypropylene, and similar polymeric materials.

As shown in the examples of the device 10, a recessed area 14 adapted in shape to accommodate the hand and wrist of a patient, may be formed into one, or opposing surfaces of the mount 12. The material forming the mount 12 may be of a denier which will allow for a comfortable positioning of the hand of a patient in the recessed area 14 for the duration of the surgical procedure. Silicone for example can be formed in a denier which slightly compresses under weight and would allow for a cradling engagement of a hand in the recessed area 14 and soft comfortable support. Silicone is also adapted to undergo the heat of conventional steam sterilization or other sterilization so that the mount 12 can be packaged in a sealed container such as a plastic envelope (not shown) to maintain the sterility of the instruments engaged with the mount 12 and the mount 12 itself.

In certain examples, pre-engaged to the mount 12 are one or a plurality of restraints such as the depicted elastic or strap restraints 16. At least one end of each restraint 16 may be connected to the surface of the mount 12 by a removable connector 18. In examples, such connectors may be snaps, buttons, magnets, screws, or other separable removable connectors 18 as one skilled in the art may employ such as any from the 2018 GRAINGER catalog. If the restraints 16 are elastic, then the connector 18 may be fixed since the restraints 16 may be stretched to insert the hand of a patient into the recessed area 14 and thereafter removed therefrom. The restraints 16 so positioned may be adapted to contact and restrain the hand and wrist of a patient, within the recessed area 14 for the duration of the surgical procedure. The hand of the patient is thus secured from moving which as noted can have catastrophic consequences during a procedure with scalpels and other surgical instruments being employed. While not shown, the mount 12 itself may be secured to the surgical table using conventionally available straps and the like for such securement.

Additionally shown in FIGS. 1-2, are the inclusion of removable engaged surgical instruments 20 which may be engaged to the mount 12 as a kit. Each kit of instruments 20 may include a plurality of specific instruments 20 which are employed by surgeons for a specific surgery. Such as shown may include a guide, pick-ups, blade or scalpel, release blades, elevators, or other instruments specifically employed in an individual specific surgical procedure.

The device 10 with a kit of instruments 20 specific to a surgical procedure, may be labeled on the exterior as to the procedure or procedures the device 10 with the included kit of instruments 20 is adapted to perform. The surgical support staff thus need only find the device 10 labeled on the exterior with indicia indicating the particular device 10 chosen matches the surgical procedure for which it is being chosen.

Shown in FIG. 2 is an example of the device 10 having thumb recesses 22 on opposing sides of the recess for the palm and fingers of the hand of a patient. This example of the device 10, thus on a single surface of the mount 12, provides for fixed positioning of either the right hand or left hand of a patient within the recess 14 in the mount 12. Restraints 16 may also be provided to secure and hold either hand in the recess 14 and in a fixed position for the duration of the procedure.

Shown in FIG. 3, is another example of the device 10 herein adapted for either the right or left hand of the user. As depicted, a second recess 14 is formed into a rear surface 24 of the mount 14 for the opposite hand of the recess 14 formed into the front surface 26 of the mount 12. The restraints 16 can be moveable between the front surface 26 and rear surface 24, or simply provided engaged to both surfaces. Removable connectors 18 are employed unless the restraints are elastic wherein they may be in fixed engagement to the mount 12.

In examples of the device 10 shown, a drape cloth 28 may be included. The drape cloth 28 may be in a fixed engagement to the mount 12 on one end. Alternatively, the drape cloth 28 may be removably adhered to the mount 12 such as with a separable adhesive 30.

Figure 4:
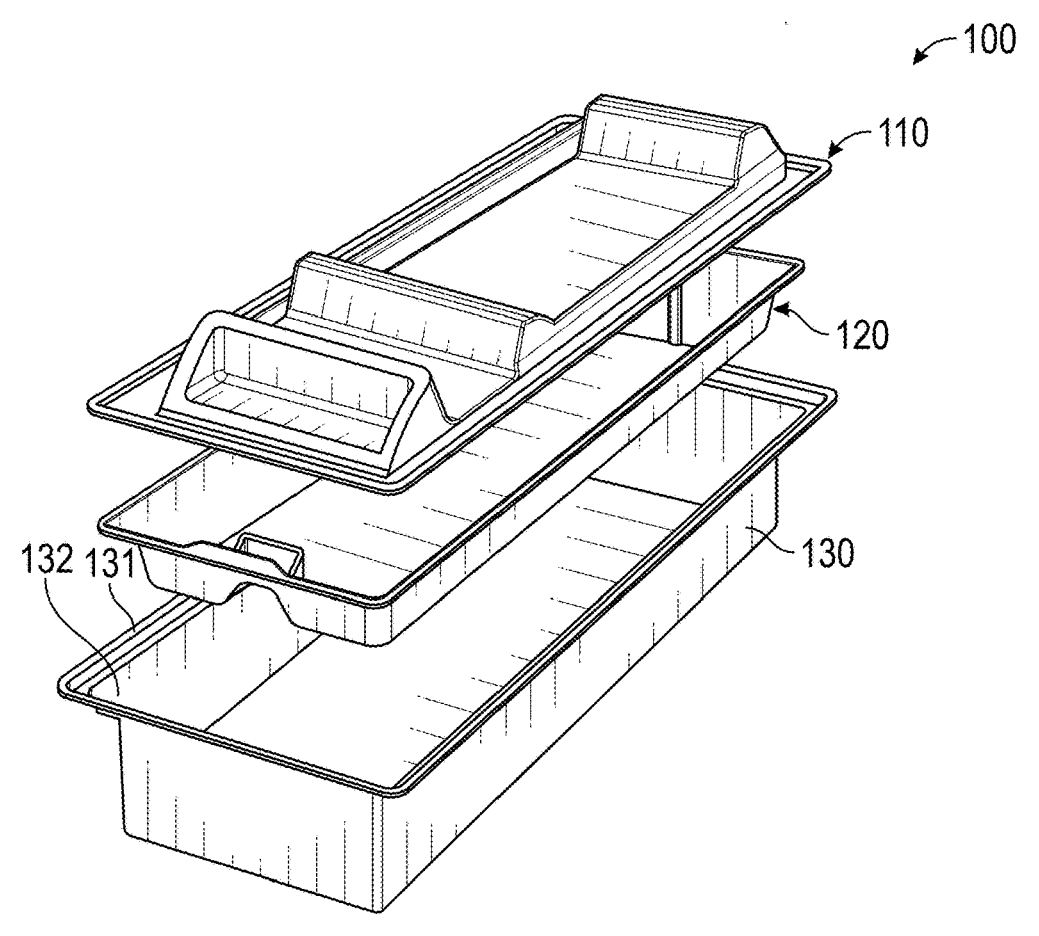
FIG. 4 illustrates an exploded view of a hand positioning tray device.

FIG. 4 illustrates an exploded view of an example of a hand/wrist positioning surgical kit or device 100. The hand/wrist positioning surgical kit 100 can include a top tray 110, a middle tray 120, and a bottom tray 130. The three trays can be configured to fit within one another. The bottom tray 130 can receive the middle tray 120. The bottom tray 130 and/or the middle tray 120 can receive the trop tray 110. Other configurations may include only one tray or two trays, such as a bottom tray 130 and top tray 110. Some configurations may include more than three trays configured to fit together or nest within one another. The top tray 110 may be configured as a handhold, dimensioned to receive a patient's hand in the correct position. The top tray 110 may be positioned on a table, such as a medical examination table. The top tray 110 may be used to securely position and hold a patient's hand in place for a medical procedure. The middle tray 120 and/or bottom tray 130 can also hold a variety of tools or instruments for use in the medical procedure.

In some configurations, the lip or edge of the bottom tray 130 may have a first groove or recess 132 to receive a middle tray 120. The middle tray 120 can include a protrusion or edge that can fit into the corresponding first groove 132 of the bottom tray 130. Similarly, the lip or edge of the bottom tray 130 may have a second groove or recess 131 to receive the top tray 110. The top tray 110 can also have a protrusion or edge that can fit into the corresponding second groove 131 of the bottom tray 130. The second groove or recess 131 may be positioned above the first groove or recess 132. The second groove or recess 131 may have a longer length and/or width than the length and/or width of the first groove or recess 132. In some configurations, the middle tray 120 can include a groove to receive the top tray 110. The top tray 110 can include a protrusion or edge that can fit into the corresponding groove of the middle tray 120.

In some configurations, the bottom tray 130 may have a series of inwardly extending protrusions or projections configured to receive or support a bottom surface of the middle tray 120 and/or the top tray 110. Similarly, in some configurations, the middle tray 120 may have a series of inwardly extending protrusion or projections configured to receive or support a bottom surface of the top tray 110. The middle tray 120 and/or top tray 110 may be interference fit with the bottom tray 130. The middle tray 120 may also be interference fit with the top tray 110. The middle tray 120 and/or top tray 110 have protrusions or features that create an interference fit with the bottom tray 130. In some configurations, the bottom tray 130 may have protrusions of features that create an interference fit with the received middle tray 120 and/or top tray 110. Each of the trays may be made of a semi-rigid material.

Figure 5:
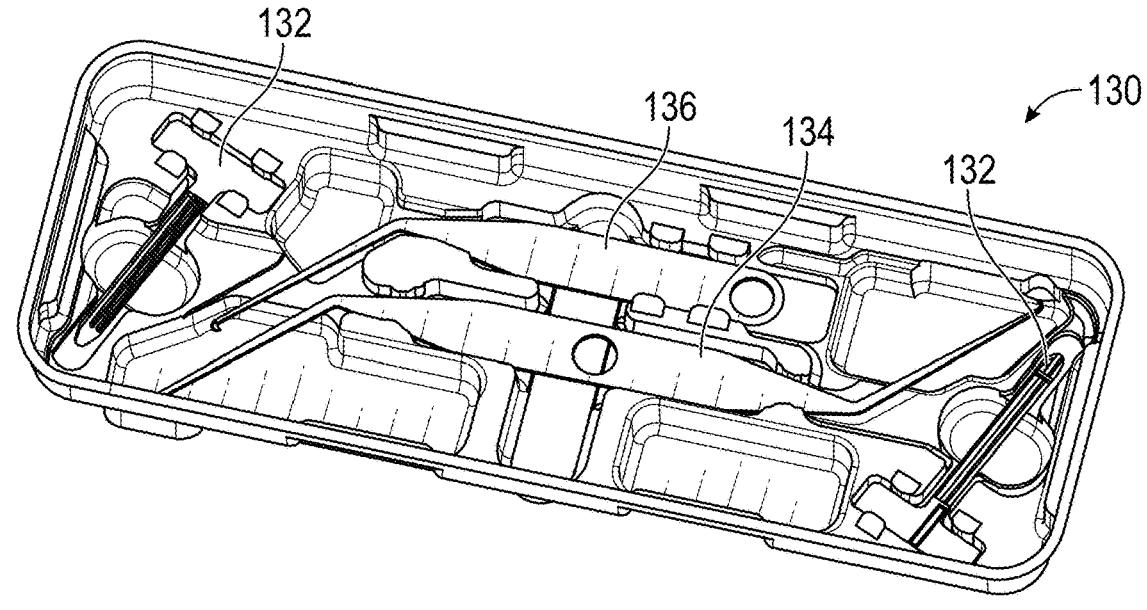
FIG. 5 illustrates a bottom tray of the hand positioning tray device of FIG. 4.

FIG. 5 illustrates an example of a bottom tray 130 of the hand/wrist positioning surgical kit 100 of FIG. 4. The bottom tray 130 may hold or store a plurality of a variety of instruments. For example, the bottom tray 130 illustrated in FIG. 5 includes two guides 132, a retrograde blade 136, and a combination probe or rasp instrument 134. The surface of the bottom tray 130 may include a series of customizable recesses to receive the individual instruments. These recesses can securely hold the individual instruments in place, particularly when the hand/wrist positioning surgical kit 100 is moved. The recesses can also separate the individual instruments to hold them apart from one another. As described herein, the middle tray 120 may be received by the bottom tray 130. The recesses of the bottom tray 130 may allow the instruments to rest below the surface of the bottom tray 130, such that the middle tray 120 does not come into contact with the instruments when positioned within the recesses of the bottom tray 130. Additionally, the recesses can be shaped and dimensioned to not only receive each instrument, but also to allow a user to easily grip and remove each instrument from the corresponding recess.

Figure 6:
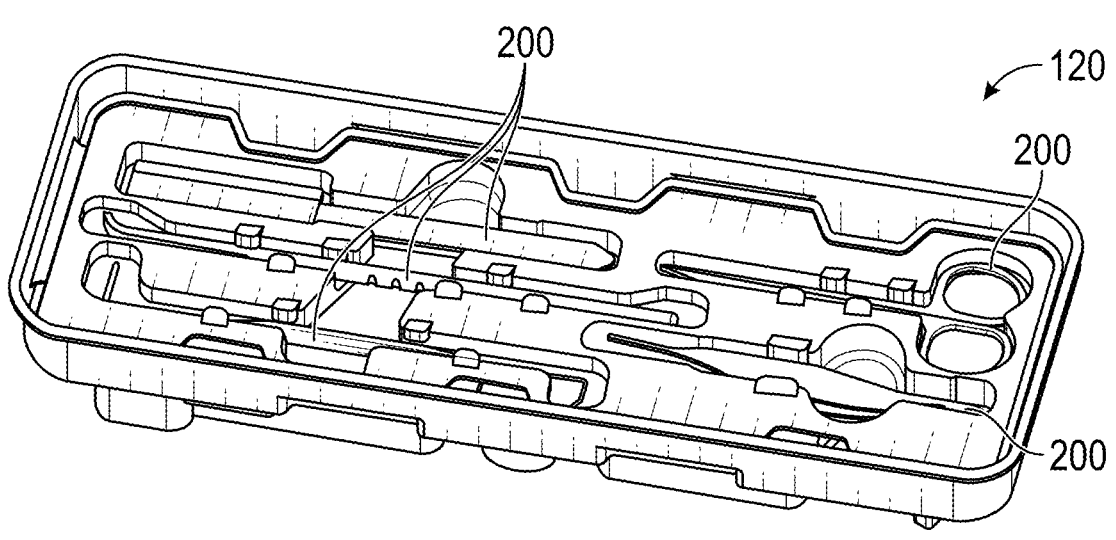
FIG. 6 illustrates a middle tray of the hand positioning tray device of FIGS. 4 and 5.

FIG. 6 illustrates an example of a middle tray 120 of the hand/wrist positioning surgical kit 100 of FIGS. 4 and 5. Similar to the bottom tray 130, the middle tray 120 may hold a plurality of a variety of instruments. For example, the middle tray 120 illustrated in FIG. 6 includes a plurality of instruments 200, such as scalpel blades, scissors, forceps, dilator or elevator tool, and retractors. Also similar to the bottom tray 130, the middle tray 120 may have a series of recesses that can be customizable to receive individual instruments. As discussed herein, the middle tray 120 may be received by the bottom tray 130. Similarly, the middle tray 120 may receive the top tray 110.

Figure 7A:
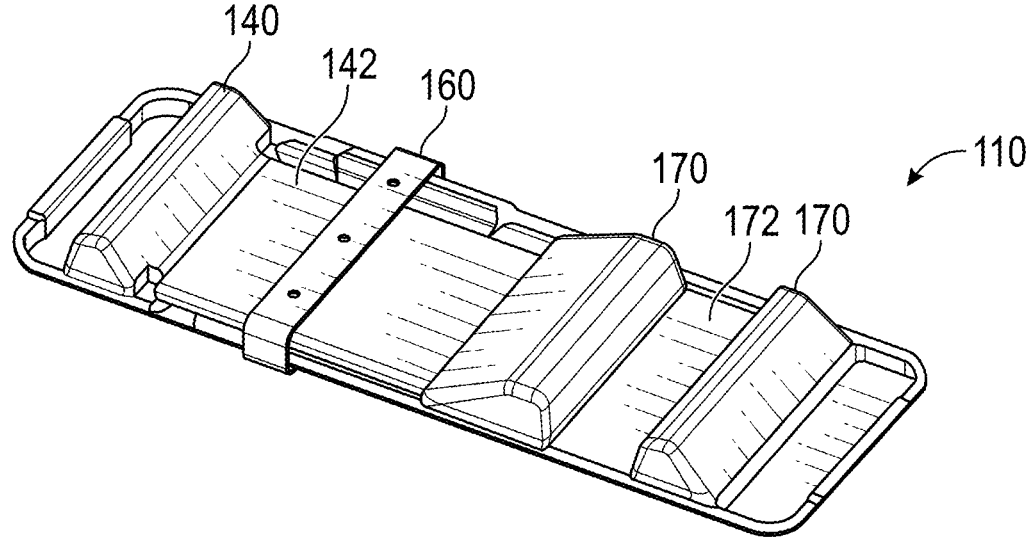
FIG. 7A illustrates a top tray of the hand positioning device of FIGS. 4-6.
Figure 7B:
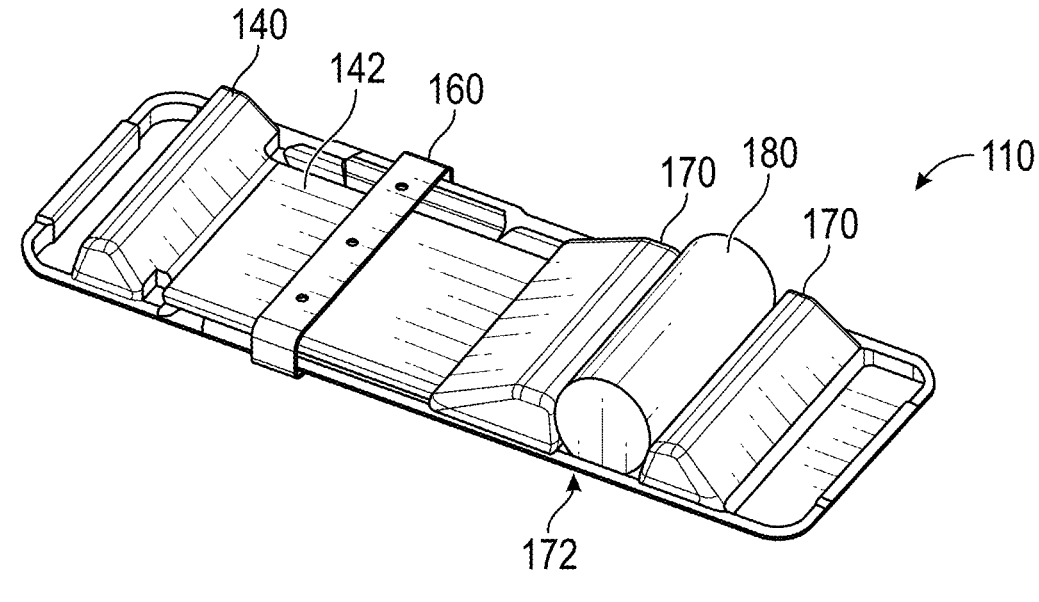
FIG. 7B illustrates the top tray of FIG. 7A with a roll positioned thereon.
Figure 8:
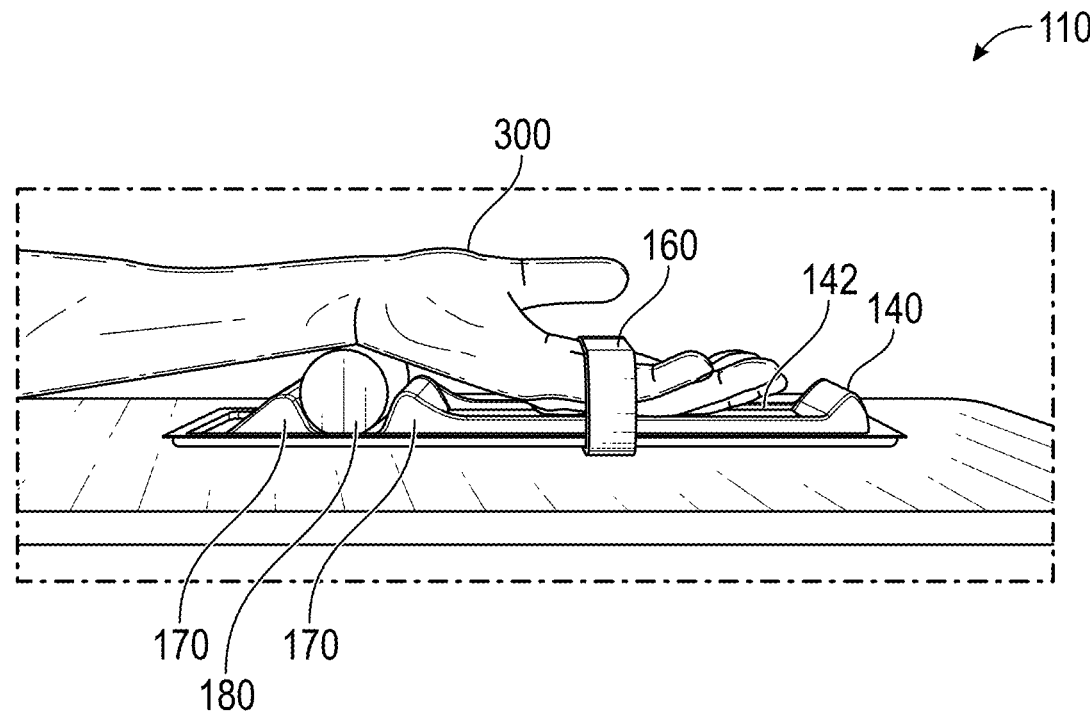
FIG. 8 illustrates the top tray of FIGS. 7A-7B with a hand positioned thereon.

FIG. 7A illustrates a top tray 110 of the hand/wrist positioning surgical kit 100. FIG. 7B illustrates the top tray 110 with a roll 180 positioned thereon for positioning the hand and wrist. FIG. 8 illustrates the hand/wrist positioning top tray 110 with a hand/wrist 300 positioned thereon. The top tray 110 may be used as a mount to position and restrain a hand/wrist 300 in place for a procedure, as shown in FIG. 8. The top tray 110 may have a hand recess 142. The hand recess 142 may be dimensioned to receive and position the patient's hand 300. The patient's hand 300 may be positioned palms up on the top tray 110 of the kit 100, with the patient's hand within the hand recess 142. The top tray 110 can include a strap 160, which may be elastic or elastomer, to restrain the hand 300 in position within the hand recess 142. The strap 160 may be positioned over the top surface of the hand 300, as illustrated in FIG. 8. The strap 160 can be positioned over the fingers of the patient's hand 300. The strap 160 may be adjustable such that the length can be adjusted depending on the size of the patient's hand 300. The position of the strap 160 may also be adjustable along the length of the top tray 110, such that the strap 160 can be adjusted depending on the size of the patient's hand 300.

The trop tray 110 may also have one or more elevated portions or protrusions 170. The one or more elevated portions 170 can be positioned at the proximal end of the top tray 110. The one or more elevated portions 170 may be configured to position and stabilize the patient's wrist. The one or more elevated portions 170 can have a recess 172 positioned there between. The recess 172 may receive a roll 180, as shown in FIGS. 7B and 8. The roll 180 may be a roll of bandages or esmark bandages. The elevated portions 170 may be sloped for comfort of the patient, to allow the patient's wrist to be supported by the one or more elevated portions 170 and to allow the patient's hand 300 to rest within the hand recess 142. The top tray 110 can also have a second elevated portion 140, which can be positioned at the distal end of the top tray 110. The second elevated portion 140 can act to barrier or to form the hand recess 142. The second elevated portion 140 can act to position and retain the patient's hand 300 within the hand recess 142. The hand recess 142 may be a substantially flat surface between the one or more elevated portions 170 at one end of the top tray 110 and the second elevated portion 140 at the other end of the top tray 110.

In examples, the combination probe or rasp instrument 134 illustrated in the bottom tray in FIG. 5 may be a dual sided medical instrument. The handle may be substantially straight and sized for gripping by the fingers and hands of a surgeon. The handle may be formed in a unitary structure with both the rasp positioned at a first end and a probe positioned at an opposite end. In examples, the handle may be formed independently of the two different instruments extending from opposite ends thereof such as by forming it of a plastic or polymeric material or of metal, which is adapted at both ends to operatively engage with the chosen surgical instruments.

In examples, at a first end of the formed handle portion extends a first instrument having a proximal end adapted to engage the handle and having a distal end configured as the surgical instrument such as a probe. At the opposite second end of the handle may extend the second instrument from a proximal end thereof adapted to engage the second end of the handle. The second instrument may extend to a distal end on which the second instrument is formed, such as a probe.

In examples of the device, a central portion of the first instrument and a central portion of the second instrument, extend from the ends of the handle at an angle substantially between approximately 20 to 60 degrees, such as between 20 to 40 degrees, 30 to 50 degrees, 40 to 60 degrees, 20 to 45 degrees, 45 to 60 degrees, 20 to 30 degrees, 30 to 40 degrees, 40 to 50 degrees, 50 to 60 degrees, relative to a central axis of the handle. By substantially is meant plus or minus 1 percent, 2 percent, 5 percent, 10 percent, 15 percent, or 20 percent.

In examples, this angled extension allows for the surgeon using one of the instruments extending from the handle to position the second instrument out of the way of his hand and arm as it will extend at the angle away from the handle opposite that of the first instrument.

For example, a single surgical instrument which include a first surgical tool such as a rasp on a first end and a second surgical tool such as a probe at the second end, may therefore allow the surgeon the ability to accomplish two tasks without having to change instruments.

Figure 9:
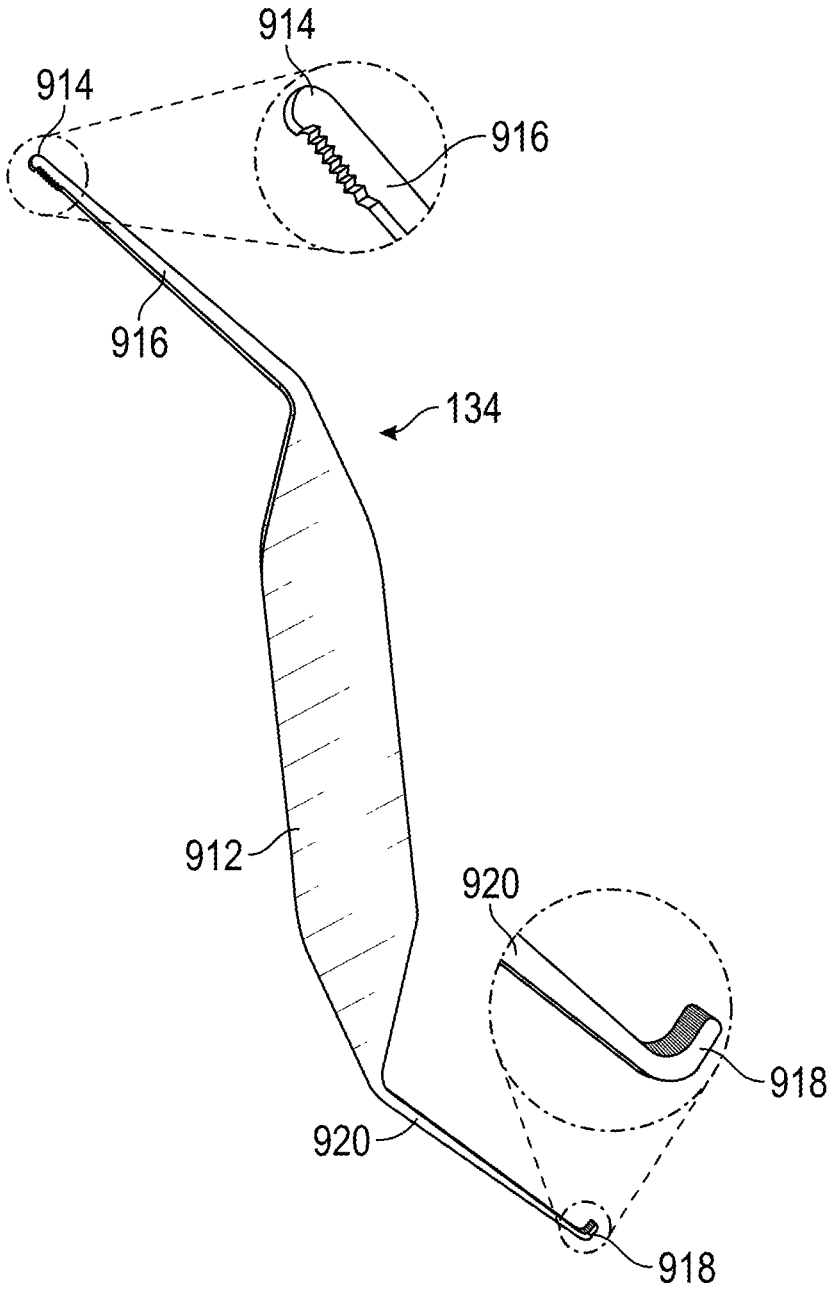
FIG. 9 shows a depiction of the surgical device herein having a centrally positioned handle portion and having a rasp extending from an angled section at a first end and having a probe extending from an angled portion at an opposite end, formed as a unitary structure.
Figure 10:
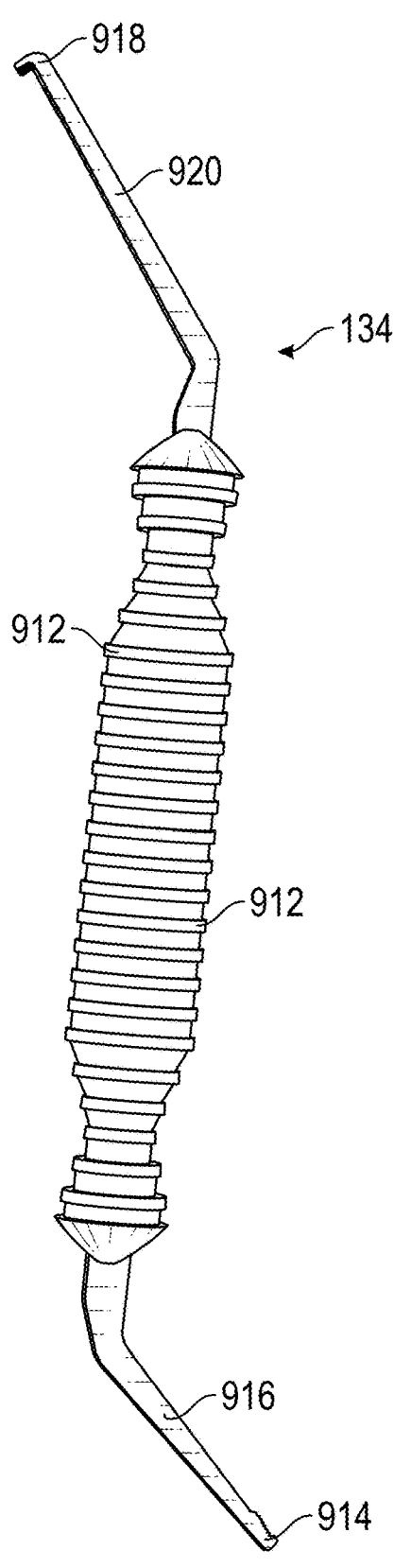
FIG. 10 depicts the device as described herein having the rasp at a first end of a centrally located handle and having the probe at an opposing end and having a centrally located handle formed in a cylindrical shape which ridges on opposing sides of recesses to provide enhanced gripping of the handle and comfort.

Referring now to the drawings in FIGS. 9-10, there is seen in FIG. 9, one example of the device 134 herein formed in a unitary structure of material such as stainless steel. As shown, the device 134 may have a centrally positioned handle 912 which as shown is substantially planar and adapted for compression holding between the fingers and thumb of the user. At a first end of the handle may extend a first surgical tool, and at an opposing end of the handle 912 extends a second surgical tool.

The first surgical tool may include a rasp 914 positioned at the distal end of a first projecting member 916. The proximal 915 end of the first projecting member 916 is engaged to the first end of the handle 912. The second surgical tool includes a probe 918, positioned at the distal end of a second projecting member 920. The proximal end of the second projecting member 920 is engaged to 920 the second end of the handle 912.

In examples of the device 134 herein, both the first projecting member 916 and the second projecting member 920 may extend from their respective engagements to the handle 912 ends, at opposing angles. Currently, in the example, the angle of extension relative to the central axis of the handle 912 (FIG. 10) is between 20 to 60 degrees with an angle of between substantially 40-50 degrees, 20 to 40 degrees, 30 to 50 degrees, 40 to 60 degrees, 20 to 45 degrees, 20 to 30 degrees, 30 to 40 degrees, 40 to 50 degrees, or 50 to 60 degrees.

Shown in FIG. 10, an example of device 134 is shown with the rasp 914 extending from the handle 912 engaged with the first projecting member 916 at a first end. Also shown is the probe 918 at the distal end of the second projecting member 920 extending from the opposite end of the handle 912. As shown, the first and second projecting members extend in opposite directions at an angle between 40-60 degrees.

In this example, the handle 912 may be formed independent of the two surgical tools extending from opposite ends thereof. As shown, the centrally located handle is formed in a cylindrical shape which ridges on opposing sides of recesses extending along the handle 912. This combination of ridges and recesses provides enhanced gripping of the handle and more comfort during use.

The handle 912 may be formed of a material adapted to not survive the rigors of steam sterilization so to prevent re-use and only be compatible with EO or Gamma sterilization. Such, for example, may be a polymeric material with a melting temperature below 220 F degrees such as polyethylene or other materials. In this example the shore of the material may be formed in a durometer allowing for slight compression during use by the surgeon, to provide additional comfort and a more secure grip.

While all of the fundamental characteristics and features of the dual use surgical implement invention have been shown and described herein, with reference to particular embodiments thereof, a latitude of modification, various changes and substitutions are intended in the foregoing disclosure and it will be apparent that in some instances, some features of the invention may be employed without a corresponding use of other features without departing from the scope of the invention as set forth. It should also be understood that various substitutions, modifications, and variations may be made by those skilled in the art without departing from the spirit or scope of the invention. Consequently, all such modifications and variations and substitutions are included within the scope of the invention as defined by the following claims.

While all of the fundamental characteristics and features of surgical kit and hand/wrist positioning surgical kit have been shown and described herein, with reference to particular embodiments thereof, a latitude of modification, various changes and substitutions are intended in the foregoing disclosure and it will be apparent that in some instances, some features of the invention may be employed without a corresponding use of other features without departing from the scope of the invention as set forth. It should also be understood that various substitutions, modifications, and variations may be made by those skilled in the art without departing from the spirit or scope of the invention. Consequently, all such modifications and variations and substitutions are included within the scope of the invention as defined by the following claims.

What is claimed is:

1. A combination surgical kit comprising:
a plurality of tools for a medical procedure, the plurality of tools comprising a first set of tools and a second set of tools; and
a hand/wrist positioning tray device comprising:
a bottom tray configured to hold the first set of tools;
a middle tray configured to hold the second set of tools; and
a top tray comprising a substantially flat surface and an elevated portion including
a recess configured to receive a roll of bandages,
wherein the substantially flat surface is configured and dimensioned to receive a hand of a patient for the medical procedure, and
wherein the elevated portion is configured to support the wrist of the hand for the medical procedure.

2. The combination surgical kit of claim 1, wherein the first set of tools comprises one or more selected from the group consisting of: guides, a retrograde blade, and a combination probe and rasp instrument.

3. The combination surgical kit of claim 1, wherein the first set of tools comprises a combination probe and rasp instrument comprising two different surgical tools extending from respective opposing ends of a centrally located handle.

4. The combination surgical kit of claim 1, wherein the second set of tools comprises one or more selected from the group consisting of: a scalpel blade, a pair of scissors, forceps, a dilator and elevator tool, and a retractor.

5. The combination surgical kit of claim 1, wherein the bottom tray comprises a plurality of recesses configured to receive each of the first set of tools.

6. The combination surgical kit of claim 1, wherein the middle tray comprises a plurality of recesses configured to receive each of the second set of tools.

7. The combination surgical kit of claim 1, wherein the top tray comprises a strap configured to be positioned over and restrain the hand.

8. The combination surgical kit of claim 1, wherein the elevated portion comprises a sloped portion.

9. The combination surgical kit of claim 1, wherein the elevated portion comprises a first elevated protrusion on a first side of the recess and a second elevated protrusion on a second side of the recess.

10. The combination surgical kit of claim 7, wherein the strap is an elastomer strap.

11. The combination surgical kit of claim 7, wherein the strap is configured to be positioned over a portion of the arm of the patient on the substantially flat surface of the top tray.

12. A hand/wrist positioning tray device, comprising:

a bottom tray configured to hold a first set of tools;

a middle tray configured to hold a second set of tools; and a top tray comprising a substantially flat surface and an elevated portion, wherein the substantially flat surface is configured and dimensioned to receive a hand of a patient in an extended position for a medical procedure accessing the volar wrist, wherein the elevated portion further comprises a recess configured to receive a roll of bandages, and wherein the elevated portion is configured to support the wrist of the patient for the medical procedure.

13. The device of claim 12, wherein the bottom tray comprises a plurality of recesses configured to receive each of the first set of tools.

14. The device of claim 12, wherein the middle tray comprises a plurality of recesses configured to receive each of the second set of tools.

* * * * *